(12) United States Patent
Herrmann et al.

(10) Patent No.: US 8,383,418 B2
(45) Date of Patent: Feb. 26, 2013

(54) METHOD FOR OPERATING A TISSUE PROCESSOR

(75) Inventors: Udo Herrmann, Leiman (DE); Hermann Ulbrich, Bad Schoenborn (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 244 days.

(21) Appl. No.: 12/858,661

(22) Filed: Aug. 18, 2010

(65) Prior Publication Data

US 2011/0041599 A1   Feb. 24, 2011

(30) Foreign Application Priority Data

Aug. 21, 2009   (DE) .......................... 10 2009 038 481

(51) Int. Cl.
*G01N 1/36* (2006.01)
(52) U.S. Cl. .......................... 436/176; 436/174; 422/536
(58) Field of Classification Search .......................... None
See application file for complete search history.

(56) References Cited

U.S. PATENT DOCUMENTS

| 2002/0131896 A1 | 9/2002 | Hunnell et al. |
| 2007/0025179 A1 * | 2/2007 | Hildreth .......................... 366/136 |
| 2007/0243626 A1 | 10/2007 | Windeyer et al. |
| 2010/0099199 A1 | 4/2010 | Egle et al. |
| 2010/0112624 A1 | 5/2010 | Metzner et al. |

FOREIGN PATENT DOCUMENTS

| DE | 10163488 | 7/2003 |
| DE | 102008054066 | 5/2010 |
| DE | 10 2009 038 481 | 9/2011 |
| EP | 1975595 | 10/2008 |
| GB | 2472891 | 2/2012 |

OTHER PUBLICATIONS

"Leica ASP 300", Brochure, Leica Microsystems Nussloch GmbH, Order No. 0704-2-0-103, Apr. 2001.

* cited by examiner

*Primary Examiner* — Yelena G Gakh
*Assistant Examiner* — Christopher A Hixson
(74) *Attorney, Agent, or Firm* — Schlee IP International, P.C.; Alexander R. Schlee

(57) ABSTRACT

A method for operating a tissue processor is described. During the operation of a tissue processor a reagent is fed from a container into a retort of the tissue processor, which retort does not contain any tissue samples. Thereafter, the reagent is returned into the container. During feeding, returning and/or in between feeding and returning a measured value is detected by a sensor of the tissue processor. This value is representative of a concentration of the reagent. During this feeding, this returning and/or in between no tissue sample is placed in the retort.

6 Claims, 2 Drawing Sheets

METHOD FOR OPERATING A TISSUE PROCESSOR

CROSS-REFERENCE TO RELATED APPLICATION

This application claims the priority of the German patent application DE 102009038481.2 having a filing date of Aug. 21, 2009. The entire content of this prior German patent application DE 102009038481.2 is herewith incorporated by reference.

BACKGROUND OF THE INVENTION

The invention relates to a method for operating a tissue processor, in which a reagent is fed from a container into a retort of the processor.

Tissue processors are used for automatic processing of histological tissue samples. In doing so, the tissue samples are prepared for subsequent section preparation with a microtome, followed by microscopic examination. In several stages, the tissue samples are at first dehydrated, cleared, hardened and subsequently stabilized with a carrier material, for example paraffin. This takes place using different reagents to which the tissue samples are exposed. A tissue processor which allows a largely automatic processing of the samples is illustrated and described in the Leica document "Leica ASP 300", Leica Microsystems Nussloch GmbH, Order-No. 0704-2-0-103, April 2001.

For different process steps, which are executed with the aid of the tissue processor, the reagents are required in different concentrations. Partly the reagents can be bought as finished products with the required concentrations, and partly the required concentrations are self-produced, for example, by diluting the reagents, in particular a stock solution of the reagents.

Therefore, it is the object of the present invention to specify a method for operating a tissue processor, with which it can be easily checked whether a required reagent is suitable for a predetermined process step, or which method contributes to producing the reagent with the suitable concentration in an easy manner.

SUMMARY OF THE INVENTION

This and other objects of the invention are achieved by a method for operating a tissue processor, comprising: feeding a reagent from a container into a retort of the tissue processor, which retort does not contain any tissue samples; returning the reagent into the container; detecting by means of a sensor of the tissue processor during at least one of the actions of feeding, returning and in between feeding and returning a measured value that is representative of a concentration of the reagent; and refraining during the actions of this feeding, returning and in between feeding and returning from placing any tissue samples in the retort.

DETAILED DESCRIPTION OF THE DRAWINGS

According to the invention the reagent, after having been fed into the retort, is returned into the container, no tissue samples being present in the retort. During feeding, returning and/or in between, a measured value which is representative of a concentration of the reagent is detected with the aid of a sensor of the tissue processor. Neither during feeding, nor during returning nor in between, tissue samples are placed in the retort.

In this way, the tissue processor is used for the determination of the concentration of the reagent. The fact that the retort is free of tissue samples during the entire operation guarantees that the concentration of the reagent does not change during this operation. In contrast thereto, the reagent could be contaminated and its concentration could change if it came into contact with tissue samples. Thus, it can be easily checked, in particular without any further measuring instruments, whether the reagent is suitable for a predetermined process step or for producing a reagent with a predetermined concentration.

If the reagent is a stock solution for producing reagents with a lower concentration, it is checked in one development whether the reagent has a predetermined minimum concentration. If necessary, it is then determined in a preferred embodiment with which amount of diluent the reagent has to be mixed so that the resulting mixture is suitable for a predetermined process step. The corresponding mixing ratio can then be output via an output unit, for example a display.

After producing the mixture of stock solution and diluent, it is checked in a preferred embodiment whether the mixture is actually suitable for the predetermined process step. Further, if the mixture is not suitable for the predetermined process step, an amount of reagent or diluent is determined which, when added to the mixture, makes it suitable for the predetermined process step. The corresponding amount of reagent or diluent is then output via the output unit.

For the exact determination of the amount of diluent or stock solution, the reagent or the mixture is completely pumped into the retort in one development. Therein, the amount is detected with the aid of a filling level sensor and taken into account in the determination of the amount of diluent or, respectively, stock solution for producing the mixture.

In the following, the invention is explained in more detail with reference to schematic drawings.

DETAILED DESCRIPTION OF THE DRAWINGS

Identical elements are identified by the same reference signs throughout all Figures.

Figure 1:
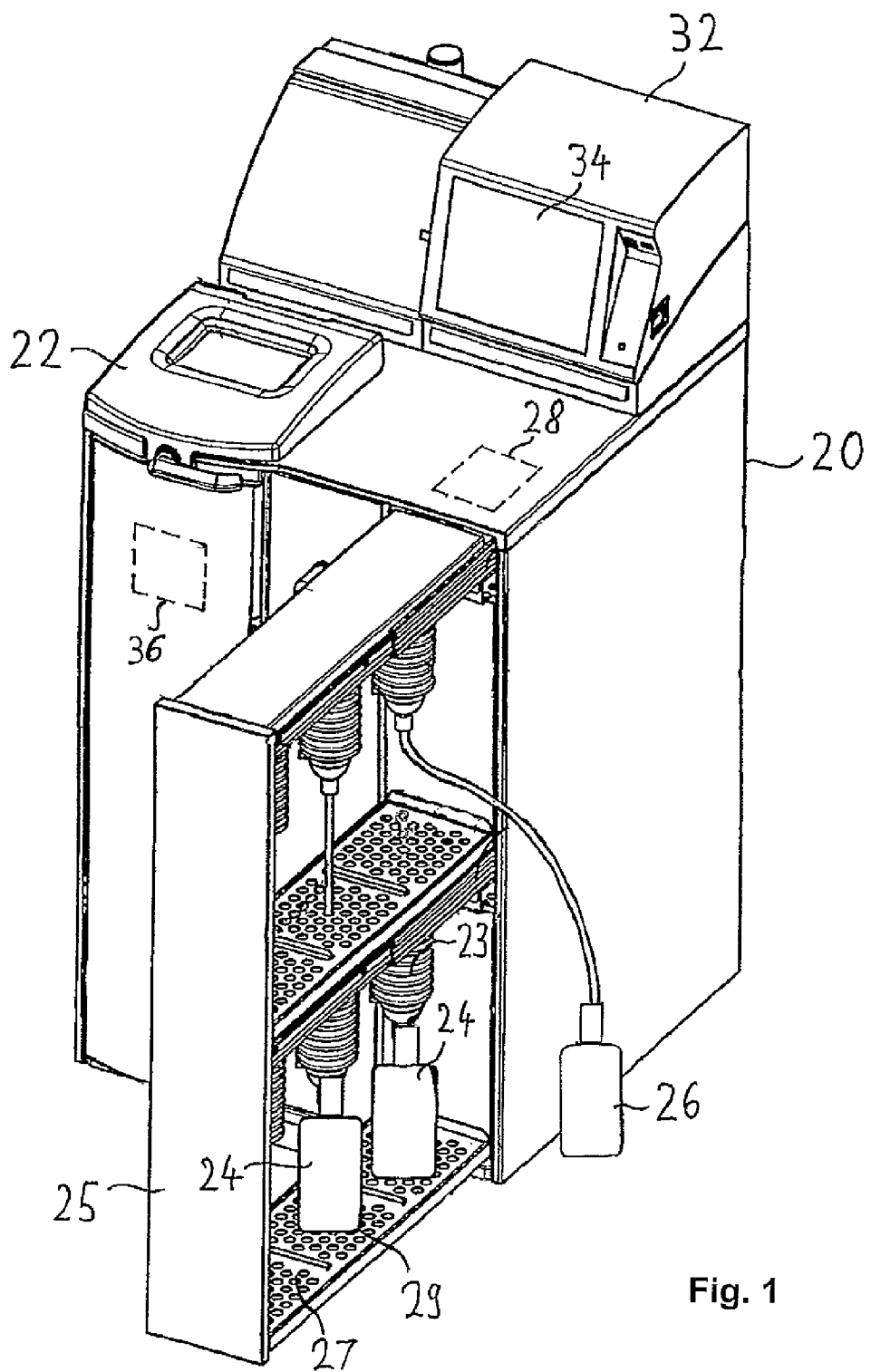
FIG. 1 shows a tissue processor.

FIG. 1 shows a tissue processor 20 having a retort 22 for processing tissue samples. Via a tubing system (not illustrated) and bellows 23, reagents are fed from internal containers 24 into the retort 22 and back. The internal containers 24 stand on bottom plates 27 having vent holes 29. The bottom plates 27 are part of a pull-out device 25 which is pulled out of the tissue processor 20 via telescopic rails. In addition to the internal containers 24, an external container 26 is connected to the tissue processor.

When feeding the reagents into the retort 22, the reagents are guided past a sensor, in particular a density sensor 28. The sensor is connected to a control unit 32. The control unit 32 has an output unit 34, in particular a display.

The reagents are dehydrating reagents, clearing reagents, intermedia, reagents for hardening the tissue samples or carrier materials. The reagents in particular comprise alcohol, xylene, or paraffin. If tissue samples are placed in the retort 22, the tissue samples are, in several process steps each, dehydrated, cleared, hardened and embedded in carrier material with the aid of the reagents. In doing so, for every single process step a specific reagent with a specific concentration is predetermined.

If no tissue samples are placed in the retort 22, the tissue processor is particularly well-suited for the determination of a concentration of the reagents, in particular of alcohol or xylene. In addition, dependent on the determined concentration further calculations can be made which facilitate work with the reagents and treatment of the tissue samples.

Figure 2:
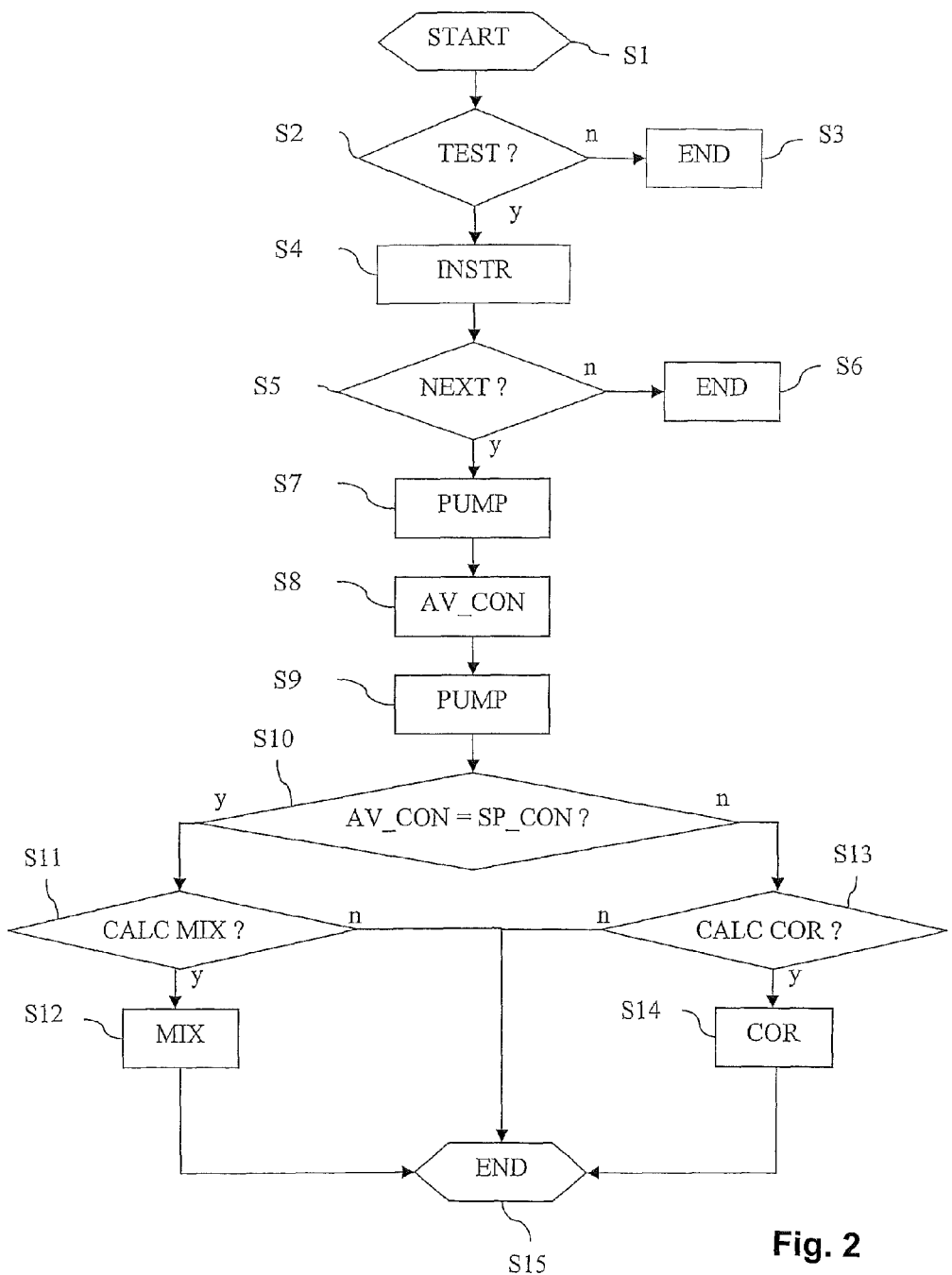
FIG. 2 shows a flow diagram for operating the tissue processor.

FIG. 2 shows a flow diagram of a program for operating the tissue processor 20, which program is stored on a storage unit of the control unit 32. The program serves to determine a concentration of the reagent and to check whether the reagent is suitable as a stock solution or for a predetermined process step, to propose a dilution by means of which a suitable concentration of the reagent for the predetermined process step can be produced, and/or to determine and output a suitable correction proposal if the reagent or the mixture is not suitable for the predetermined process step.

The program is preferably started in a step S1, for example, immediately after the start-up of the tissue processor 20. In the step S1, variables are initialized if necessary.

In a step S2, a suitability test inquiry TEST is made with the aid of which it is inquired whether the suitability of the reagent, for example alcohol or xylene, as a stock solution or for the predetermined process step is to be checked. A user of the tissue processor 20 is asked this question via the output unit 34. If the suitability test is not to be performed, the program is terminated in a step S3. If the suitability test is to be performed, the program is continued in a step S4.

In the step S4, instructions INSTR are displayed on the output unit 34. The instructions INSTR comprise that a predetermined amount of reagent or stock solution is to be filled into the internal or external containers 24, 26 without being diluted. For example, the amount is 5 l. Further, it can be indicated that the respective container 24, 26 is to be placed at a predetermined position in the pull-out device 25 or is to be connected to a predetermined external connection and/or that a suction lance is to be introduced into the respective container 24, 26.

In a step S5, it is inquired by means of a continuation inquiry NEXT whether the suitability test is to be continued. If the suitability test is not to be continued, the program can be terminated in a step S6. If the suitability test is to be continued, the program is continued in a step S7.

In the step S7, the reagent is pumped from the container 24, 26 into the retort 22 dependent on a pump instruction PUMP.

During the pump operation, a measured value AV_CON is determined in a step S8, which measured value is representative of the concentration of the reagent. The measured value AV_CON is detected by the density sensor 28.

In a step S9, the reagent is pumped back into the respective container 24, 26 by means of a further pump instruction PUMP.

During execution of the steps S7 to S9, no tissue sample is placed in the retort 22. Hereby it is guaranteed that the concentration of the reagent does not change during execution of the program. Preferably, it is displayed by means of the output unit 34 that no tissue samples may be contained in the retort 22 or may be placed in the retort.

In a step S10, it is checked whether the determined concentration is equal to a predetermined desired value SP_CON which is representative of a desired concentration. If the condition of step S10 is met, then the processing is continued in a step S11. If the condition of step S10 is not met, then the processing is continued in a step S13.

In the step S11, it is inquired by means of a calculation inquiry CALC whether a mixing ratio MIX for producing a reagent with a suitable concentration is to be performed. If the condition of step S11 is met, then the processing is continued in a step S12. If the condition of step S11 is not met, then the processing is terminated in a step S15.

In the step S12, the mixing ratio MIX is determined and output on the output unit 34. In particular, an amount of diluent is determined which has to be added to the reagent, in particular the stock solution, so that the resulting mixture is suitable for the predetermined process step. In addition to the mixing ratio MIX, the exact amount of diluent can be determined and displayed, for example in that the stock solution is completely pumped into the retort 22 and in that in the retort 22 the present amount of stock solution is determined with the aid of the filling level sensor 36. Alternatively, the present amount of stock solution can be input via a non-illustrated input unit.

In the step S13, it is inquired with the aid of a calculation inquiry CALC whether a correction ratio COR is to be determined. The correction ratio COR indicates with which amount of stock solution or diluent the mixture has to be mixed so that the resulting mixture is suitable for the predetermined process step. If the condition of step S13 is not met, then the program is terminated in the step S15. If the condition of step S13 is met, then the program is continued in a step S14.

In the step S14, the correction ratio COR is determined and output on the output unit 34.

In the step S15, the program is terminated.

The invention is not limited to the embodiments mentioned. For example, alternatively or additionally to the display, another output unit, for example a printer or an acoustic output unit can be provided. Further, the tissue processor can have more or less internal or more or less external connections for connecting internal containers 24 and external containers 26, respectively. Further, the program for operating the tissue processor can be implemented in a higher-order program. As an alternative, the program can be divided into individual subprograms so that the respective subprograms can be used exclusively for the determination of the concentration, exclusively for the determination of the mixing ratio MIX or exclusively for the determination of the correction ratio COR. Further, as an alternative to the density sensor 28 another sensor can be used for the determination of the concentration of the respective reagent.

LIST OF REFERENCE SIGNS 20 tissue processor
22 retort
24 internal container
26 external container
28 density sensor
32 control device
34 output unit
36 filling level sensor
START program start
TEST suitability test inquiry
INSTR instructions
NEXT continuation inquiry
PUMP pump instruction
AV_CON measured value
SP_CON minimum concentration
CALC calculation instruction
MIX mixing ratio
COR correction ratio END program end
S1-S15 steps one to fifteen

What is claimed is:

1. A method for operating a tissue processor, comprising:
feeding a reagent from a container into a retort of the tissue processor, which retort does not contain any tissue samples;
returning the reagent into the container;
detecting by means of a sensor of the tissue processor during at least one of the actions of feeding, returning and in between feeding and returning a measured value that is representative of a concentration of the reagent; and
refraining during the actions of this feeding, returning and in between feeding and returning from placing any tissue samples in the retort.

2. The method according to claim 1, further comprising checking dependent on the detected measured value whether the reagent has a predetermined minimum concentration.

3. The method according to claim 1, further comprising determining an amount of a diluent the reagent has to be mixed with so that the resulting mixture is suitable for a predetermined process step, and outputting the corresponding mixing ratio via an output unit.

4. The method according to claim 3, further comprising feeding the mixture of reagent and diluent into the retort and checking at the same time whether the mixture is actually suitable for the predetermined process step.

5. The method according to claim 4, further comprising determining an amount of reagent or diluent to be added for making the mixture suitable for the predetermined process step if the mixture was determined to be non-suitable for the predetermined process step, and outputting via the output unit information about the corresponding amount of reagent or diluent to be added.

6. The method according to claim 1, further comprising determining by means of a filling level sensor in the retort the actually present amount of reagent or mixture and taking this amount into account for determining the amount of diluent or reagent for creating the mixture.

* * * * *